United States Patent
O'Hare

(10) Patent No.: US 9,709,513 B2
(45) Date of Patent: Jul. 18, 2017

(54) SYSTEM AND METHOD FOR MEASURING AN OBJECT USING X-RAY PROJECTIONS

(71) Applicant: Hexagon Metrology, Inc., North Kingstown, RI (US)

(72) Inventor: Jonathan J. O'Hare, Warwick, RI (US)

(73) Assignee: Hexagon Metrology, Inc., North Kingstown, RI (US)

( * ) Notice: Subject to any disclaimer, the term of this patent is extended or adjusted under 35 U.S.C. 154(b) by 0 days.

(21) Appl. No.: 14/861,110

(22) Filed: Sep. 22, 2015

(65) Prior Publication Data

US 2016/0091439 A1 Mar. 31, 2016

Related U.S. Application Data

(60) Provisional application No. 62/057,488, filed on Sep. 30, 2014.

(51) Int. Cl.
| | |
|---|---|
| *G06K 9/00* | (2006.01) |
| *G01N 23/04* | (2006.01) |
| *G01B 15/00* | (2006.01) |
| *G06T 17/20* | (2006.01) |

(52) U.S. Cl.
CPC ........... *G01N 23/046* (2013.01); *G01B 15/00* (2013.01); *G06T 17/20* (2013.01); *G01N 2223/645* (2013.01)

(58) Field of Classification Search
CPC ...... G01N 23/046; G01B 15/00; G01B 15/04; G06T 17/20; G21K 5/10
See application file for complete search history.

(56) References Cited

U.S. PATENT DOCUMENTS

| | | | | |
|---|---|---|---|---|
| 6,694,163 | B1 | 2/2004 | Vining | 600/407 |
| 6,890,098 | B2 * | 5/2005 | Rosner | G01N 23/04 |
| | | | | 378/196 |
| 7,006,084 | B1 * | 2/2006 | Buss | G05B 19/408 |
| | | | | 345/419 |
| 7,203,267 | B2 | 4/2007 | De Man et al. | 378/4 |
| 7,254,209 | B2 * | 8/2007 | Zhao | G06T 11/006 |
| | | | | 378/4 |

(Continued)

OTHER PUBLICATIONS

International Searching Authority, International Search Report—International Application No. PCT/US2015/051838, dated Nov. 26, 2015, together with the Written Opinion of the International Searching Authority, 11 pages.

*Primary Examiner* — Gregory M Desire
(74) *Attorney, Agent, or Firm* — Sunstein Kann Murphy & Timbers LLP

(57) ABSTRACT

An apparatus and method of measuring an object (having at least two edges) projects a plurality of x-ray images of the object. At least two of the plurality of x-ray images are projected from different directions relative to the object. The apparatus and method also locate the at least two edges in the x-ray images, and ray trace a plurality of lines. Each ray traced line is tangent to at least one point on at least one of the located edges. Next, the apparatus and method reconstruct at least a partial wireframe model of the object from the tangent points of the ray traced lines. The wireframe model includes the at least two edges. Finally, the apparatus and method measure between the at least two edges of the at least partial wireframe model.

21 Claims, 9 Drawing Sheets

(56) References Cited

U.S. PATENT DOCUMENTS

| | | | |
|---|---|---|---|
| 8,638,446 B2* | 1/2014 | Briggs | G01C 15/002 33/503 |
| 9,036,770 B2* | 5/2015 | Funk | G01N 23/046 378/16 |
| 2005/0105682 A1* | 5/2005 | Heumann | G01N 23/046 378/58 |
| 2006/0002504 A1 | 1/2006 | De Man et al. | 378/4 |
| 2008/0018643 A1 | 1/2008 | Feilkas et al. | 345/420 |
| 2010/0140485 A1* | 6/2010 | Mishra | H04N 5/32 250/363.1 |
| 2011/0102430 A1* | 5/2011 | Eberhard | G06T 11/008 345/420 |
| 2012/0057174 A1* | 3/2012 | Briggs | G01C 15/002 356/603 |
| 2013/0030773 A1 | 1/2013 | O'Hare | 703/1 |
| 2013/0094735 A1* | 4/2013 | Zamyatin | G06T 11/005 382/131 |
| 2013/0188042 A1 | 7/2013 | Brooksby et al. | 348/135 |
| 2013/0195239 A1* | 8/2013 | O'Hare | G01T 7/005 378/4 |
| 2013/0279645 A1 | 10/2013 | Liesenfelt et al. | 378/12 |
| 2014/0212018 A1* | 7/2014 | Hein | G06T 11/008 382/132 |
| 2014/0368500 A1* | 12/2014 | O'Hare | G01B 15/04 345/420 |
| 2016/0091439 A1* | 3/2016 | O'Hare | G01N 23/046 378/4 |

* cited by examiner

SYSTEM AND METHOD FOR MEASURING AN OBJECT USING X-RAY PROJECTIONS

PRIORITY

This patent application claims priority from provisional U.S. patent application Ser. No. 62/057,488, filed Sep. 30, 2014, entitled, "SYSTEM AND METHOD FOR MEASURING AN OBJECT USING X-RAY PROJECTIONS," and naming Jonathan J. O'Hare as inventor, the disclosure of which is incorporated herein, in its entirety, by reference.

FIELD OF THE INVENTION

The invention generally relates to metrology and, more particularly, the invention relates to measuring between specified features of an object using an x-ray projection of the object.

BACKGROUND OF THE INVENTION

Coordinate measuring machines (CMMs) have been used for many years to accurately measure a wide variety of work pieces. For example, CMMs can measure critical dimensions of aircraft engine components, surgical tools, and gun barrels. Precise and accurate measurements help ensure that their underlying systems, such as an aircraft in the case of aircraft components, operate as specified.

Recently, those in the art have begun using computed tomography (CT) systems as CMMs for coordinate metrology. As known by those in the art, a CT system generates three-dimensional images of an object as a function of the attenuation of its x-rays by the object. Their growing acceptance may derive from their ability to obtain details about an object in a way that does not affect or otherwise damage the object.

High production manufacturing, which is an anticipated use for this type of metrology technique, requires rapid dimensional inspection for statistical process control. More specifically, high production manufacturing processes often obtain quantitative results in the form of geometric dimensions, and track those dimensions over time to monitor the efficiency of a production process. To obtain those measurements, the CT system generally reconstructs the object being produced. Undesirably, the process of reconstruction requires many processing steps that handle a great deal of image data. Accordingly, CT measurement systems known to the inventor often are not useful in rapid production lines because they typically take too much time to generate a reconstruction of an object being produced.

SUMMARY OF VARIOUS EMBODIMENTS

In accordance with one embodiment of the invention, an apparatus and method of measuring an object (having at least two edges) projects a plurality of x-ray images of the object. At least two of the plurality of x-ray images are projected from different directions relative to the object. The apparatus and method also locate the at least two edges in the x-ray images, and ray trace a plurality of lines. Each ray traced line is tangent to at least one point on at least one of the located edges. Next, the apparatus and method reconstruct at least a partial wireframe model of the object from the tangent points of the ray traced lines. The wireframe model includes the at least two edges. Finally, the apparatus and method measure between the at least two edges of the at least partial wireframe model.

The at least two edges may be located by accessing a digital file containing a digital model of the object. For example, the digital file may include a computer aided design file. Some embodiments may generate a 3D image of the object using the digital file and the wireframe model, and transmit the 3D image toward a display device for display.

The object preferably is positioned in an interior chamber of an x-ray computed tomography machine. In addition, the wireframe model may be a 2D image. Alternatively, the wireframe model may be a 3D image. Sometimes, at least one of the edges is interior to the object, although at least one edge also may be exterior to the object.

The ray tracing may produce a plurality of points that each is tangent to at least one of the edges. In that case, to reconstruct the wireframe model, the apparatus and method may access information relating to the edges (e.g., from a computer aided design file of the object) and selectively connect sets of the plurality of points to produce the at least two edges in the wireframe model. For example, the plurality of points may include a first set of points and a second set of points. The first set of points may be connected to represent a first edge of the object and, in a similar manner, the second set of points may be connected to represent a second edge of the object.

In accordance with another embodiment, a system for measuring an object having at least two edges has a chamber sized to receive and contain the object, and an x-ray source within the chamber. The x-ray source is movable relative to the object within the chamber (i.e., either or both the x-ray source or the object is/are movable) and is configured to project a plurality of x-ray images of an object. At least two of the plurality of x-ray images are projected from different directions relative to the object.

The system also has an edge detector configured for locating the at least two edges in the x-ray images, and a ray tracer operatively coupled with the edge detector. The ray tracer is configured to ray trace a plurality of lines, where each ray traced line is tangent to at least one point on at least one of the located edges. The system also has a reconstruction module operatively coupled with the ray tracer and configured to reconstruct at least a partial wireframe model of the object from the tangent points of the ray traced lines. The wireframe model has the at least two edges. The system further has a ruler operatively coupled with the reconstruction module to receive the at least partial wireframe model. The ruler is configured to measure between the at least two edges of the at least partial wireframe model.

Illustrative embodiments of the invention are implemented as a computer program product having a computer usable medium with computer readable program code thereon. The computer readable code may be read and utilized by a computer system in accordance with conventional processes.

BRIEF DESCRIPTION OF THE DRAWINGS

Those skilled in the art should more fully appreciate advantages of various embodiments of the invention from the following "Description of Illustrative Embodiments," discussed with reference to the drawings summarized immediately below.

DESCRIPTION OF ILLUSTRATIVE EMBODIMENTS

In illustrative embodiments, a computed tomography ("CT") metrology system uses precisely generated edge data to measure features of interest of an object. Details of the area/volume between the edges are not necessary. Accordingly, the system should be able to much more rapidly confirm the dimensional accuracy of objects on industrial scale. Details of illustrative embodiments are discussed below.

Figure 1A:
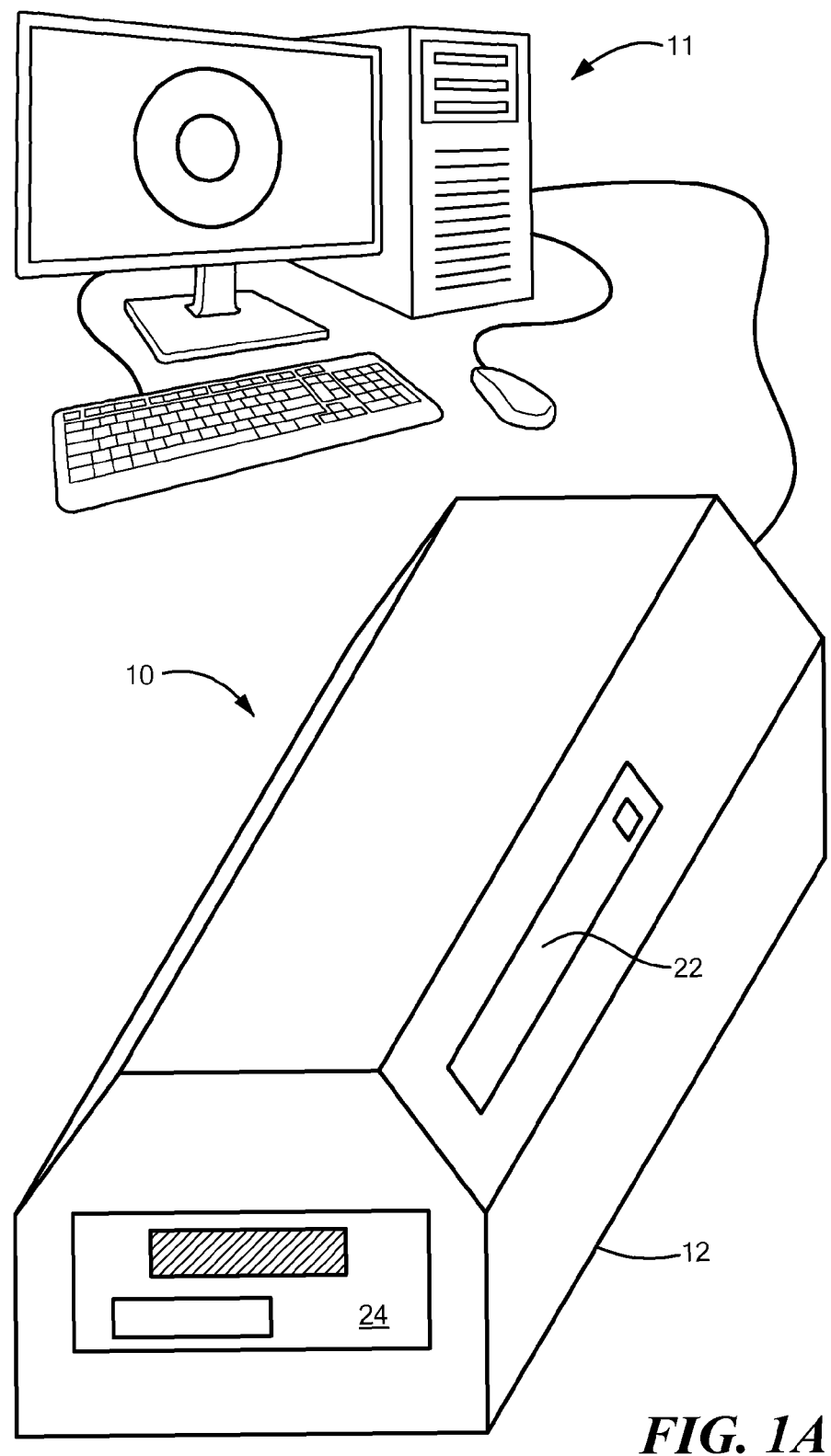
FIG. 1A schematically shows an x-ray computed tomography device that may use illustrative embodiments of the invention.
Figure 1B:
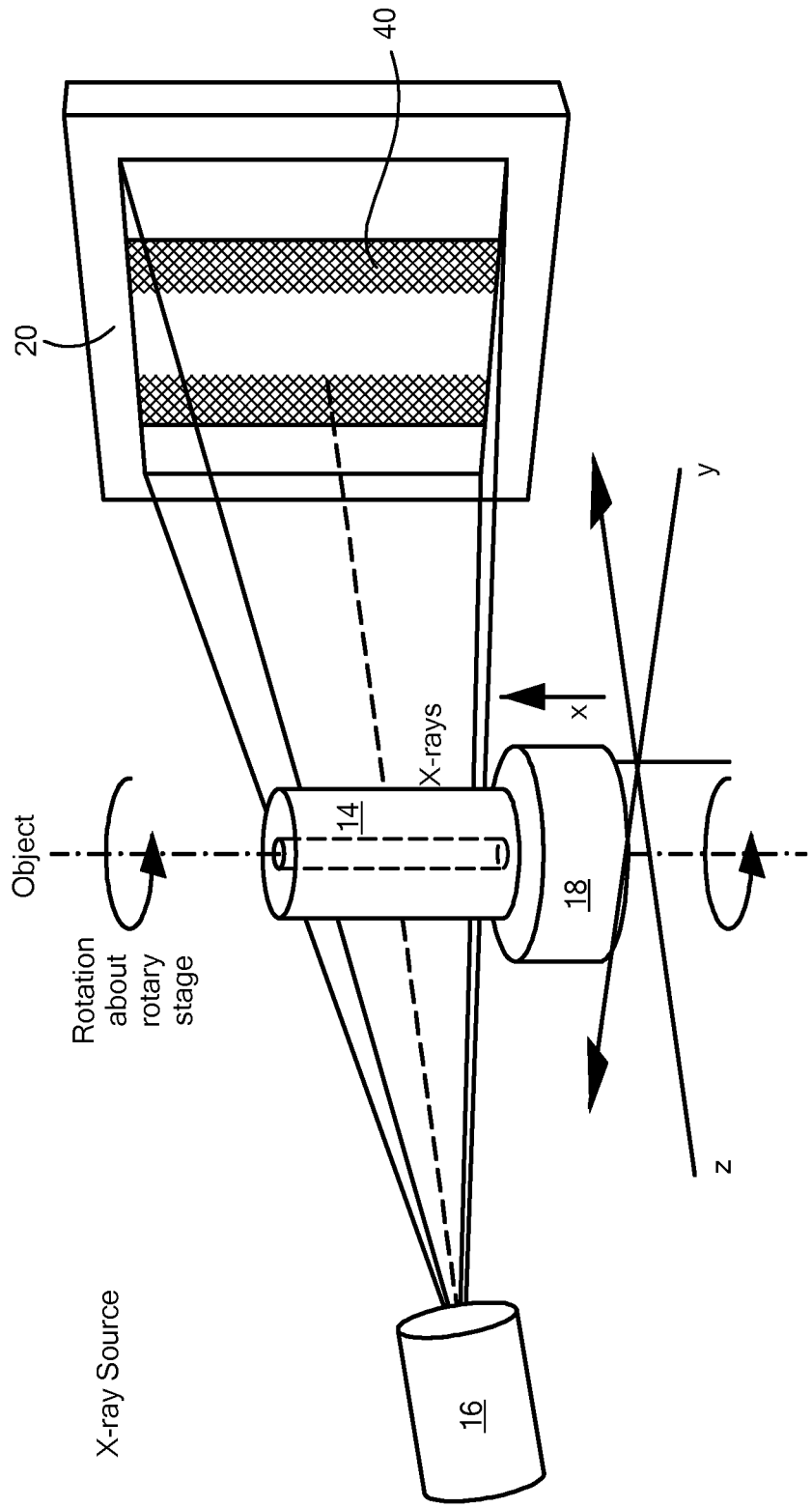
FIG. 1B schematically shows internal components of the device of FIG. 1A.

FIGS. 1 and 1B schematically show an x-ray machine/computer tomography system that may image an object of interest in accordance with illustrative embodiments. As known by those skilled in the art, the x-ray computed tomography system produces a three dimensional model of a work piece positioned within its interior (referred to as a "work piece reconstruction"). To those ends, the system includes an x-ray computed tomography machine 10 that is controlled and coordinated by some logical device, such as a computer system 11.

The computed tomography machine 10 has a housing 12 forming an interior chamber for containing, among other things (see FIG. 1B), 1) a work piece 14 (also referred to as an "object 14" or "part 14") to be measured, 2) an x-ray source 16 for generating x-rays, 3) a rotary stage 18 for supporting and rotating the work piece 14, and 4) a detector 20 for detecting the image of the work piece 14 after its image is projected onto the detector 20 by the x-ray source 16.

As noted, the work piece 14 is supported and rotated about the X-axis (from the perspective of the figures) of the rotary stage 18. Although not necessary in many instances, the work piece 14 is positioned in this figure so that it is generally co-axial with the rotary stage 18. Some work pieces 14, however, may not have such a symmetrical nominal shape and thus, cannot be positioned in this manner. For example, an irregularly shaped object may be positioned so that it rotates about some axis within its body.

An access door 22, which may be made from a transparent material, provides access to the interior for adding and removing work pieces 14. For example, the work piece 14 may be a cardiovascular stent commonly used in coronary angioplasty procedures. In addition to or instead of the computer system 11, a control panel 24 on the side of the CT machine 10 also may act as a control interface for an operator.

To produce the 3D model of the work piece 14 (the "reconstruction"), the CT system moves the work piece 14 relative to the x-ray source 16. For example, the CT system may rotate the work piece 14 a full 360 degrees on the rotary stage 18, and take/project multiple x-ray images (known in the art as "projections" or "projection angles") of the work piece 14 during rotation. During and/or after rotating the work piece 14, post-processing software executing on a local microprocessor or microcontroller (e.g., on the computer system 11) converts the data of all the projections into a 3D model of the work piece 14—the noted reconstruction. It is this 3D model—which may be a software model—that may be measured to confirm the work piece's dimensional accuracy. Thus, if the work piece 14 is a small medical device, such as a cardiovascular stent, then measurement software may precisely measure selected features of the stent, such as its diameter.

Figure 10:
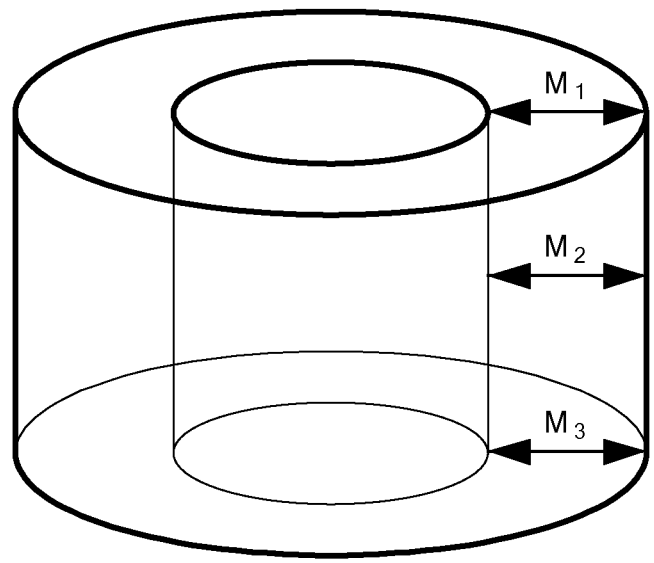
FIG. 10 schematically shows a wireframe image of the object of FIGS. 1A and 1B in accordance with illustrative embodiments of the invention.

In illustrative embodiments, this reconstruction is in the form of a wireframe drawing, thus lacking various details between the internal and/or external edges of the work piece 14. More specifically, as known by those in the art, the reconstruction preferably is a representation of the work piece 14 (a logical representation in this embodiment) specifying edges and vertices of the work piece 14. It may include exterior edges, interior edges, and hidden edges (from the perspective of exterior observers). A cube showing just its twelve edges is an example of a wireframe. The wireframe can include 2D wireframes of areas of a work piece 14, or 3D wireframes of volumes of a work piece 14. FIG. 10, discussed below, shows an example of a wireframe.

Figure 2:
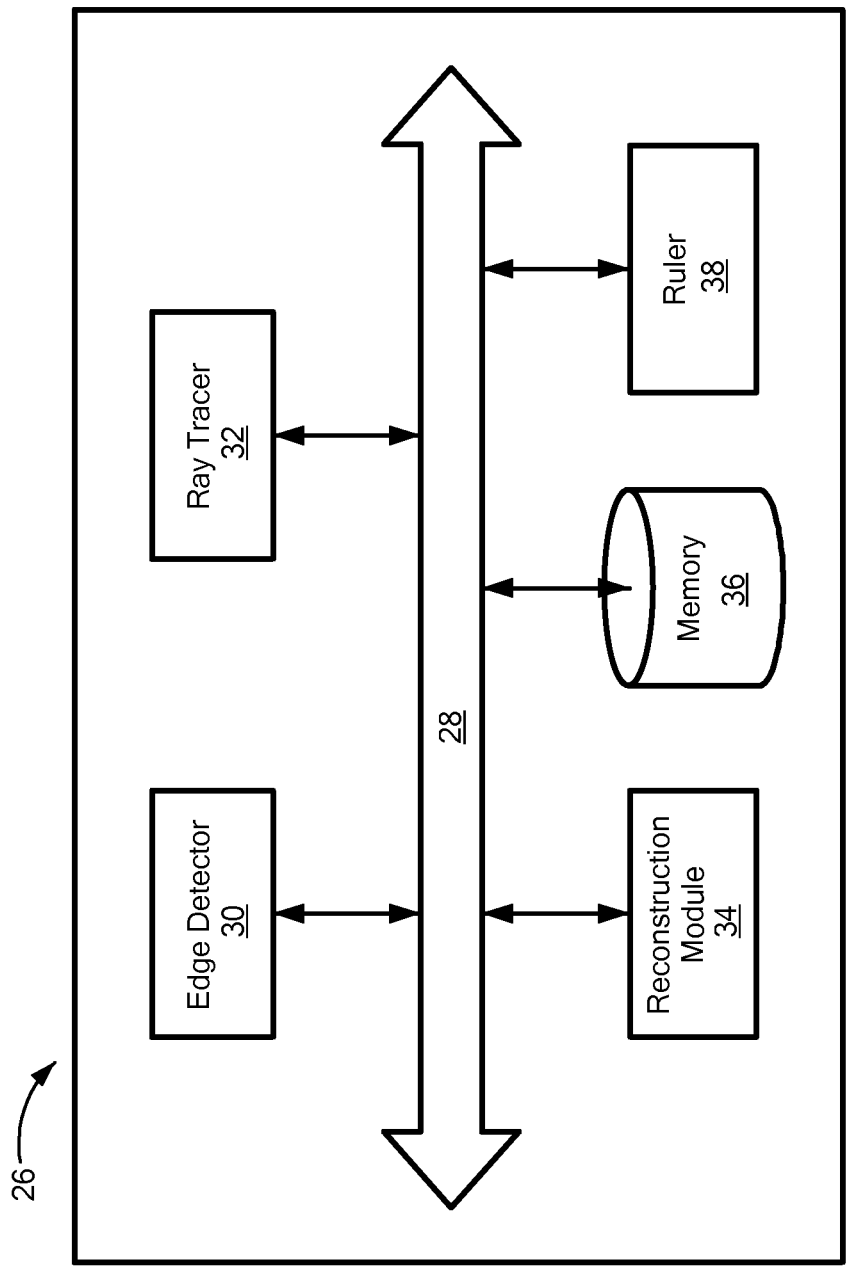
FIG. 2 schematically shows an apparatus for forming and measuring wireframe images of an object in accordance with illustrative embodiments of the invention.

FIG. 2 schematically shows an apparatus for forming and measuring wireframe images of a work piece 14 in accordance with illustrative embodiments of the invention. Among other ways, this apparatus may be implemented:

1) as a stand-alone device, 2) within the computer system 11, 3) directly into the computed tomography machine 10, and/or 4) distributed in some other way into the system.

Those skilled in the art may select the appropriate mechanism for such implementation. The apparatus includes a plurality of modules that communicate across some interconnect system to form a wireframe reconstruction of the work piece 14, and subsequently measure certain portions of the wireframe reconstructions. The interconnect system is merely shown as a bus 28, although those skilled in the art can use other known mechanisms (e.g., cables or circuit traces) for the same purpose. Accordingly, the bus 28 is included for simplicity purposes only.

Each module may be implemented as an independent unit that collaborates with at least one other of the modules, or as a plurality of different modules (e.g., distributed logic) that together delivers the desired functionality. Accordingly, discussion of a "module" is for simplicity purposes only and is not intended to limit a given module to a single hardware and/or software unit. Moreover, the apparatus can be implemented with a plurality of additional components. The modules shown in FIG. 2 thus are shown to simplify this discussion.

Those skilled in the art should understand that these components can be implemented in a variety of conventional manners, such as by using hardware, software, or a combination of hardware and software, across one or more other functional components. For example, the ray tracer (discussed below) may be implemented using a plurality of microprocessors executing firmware. As another example, the ray tracer may be implemented using one or more application specific integrated circuits (i.e., "ASICs") and related software, or a combination of ASICs, discrete electronic components (e.g., transistors), and microprocessors. Accordingly, the representation of the ray tracer and other components in a single box of FIG. 2 is for simplicity purposes only.

Among other things, the apparatus includes an edge detector 30 for detecting edges of a projection of the work piece 14 (i.e., to detect edges on a translucent x-ray image of the work piece 14), and a ray tracer 32 for projecting a ray tangent to at least one edge of the work piece 14. The apparatus also includes a reconstruction module 34 for reconstructing at least a wire frame (reconstruction) representation of the work piece 14 from the data gleaned by the ray tracer 32, and memory 36 for storing the output of the various modules (e.g., a reconstruction or data relating to the edge) or nominal data relating to the work piece 14 (e.g., computer aided design ("CAD") data). A ruler 38 logically measures the wireframe representation of the work piece 14 to confirm the dimensional accuracy of the work piece 14.

Figure 3:
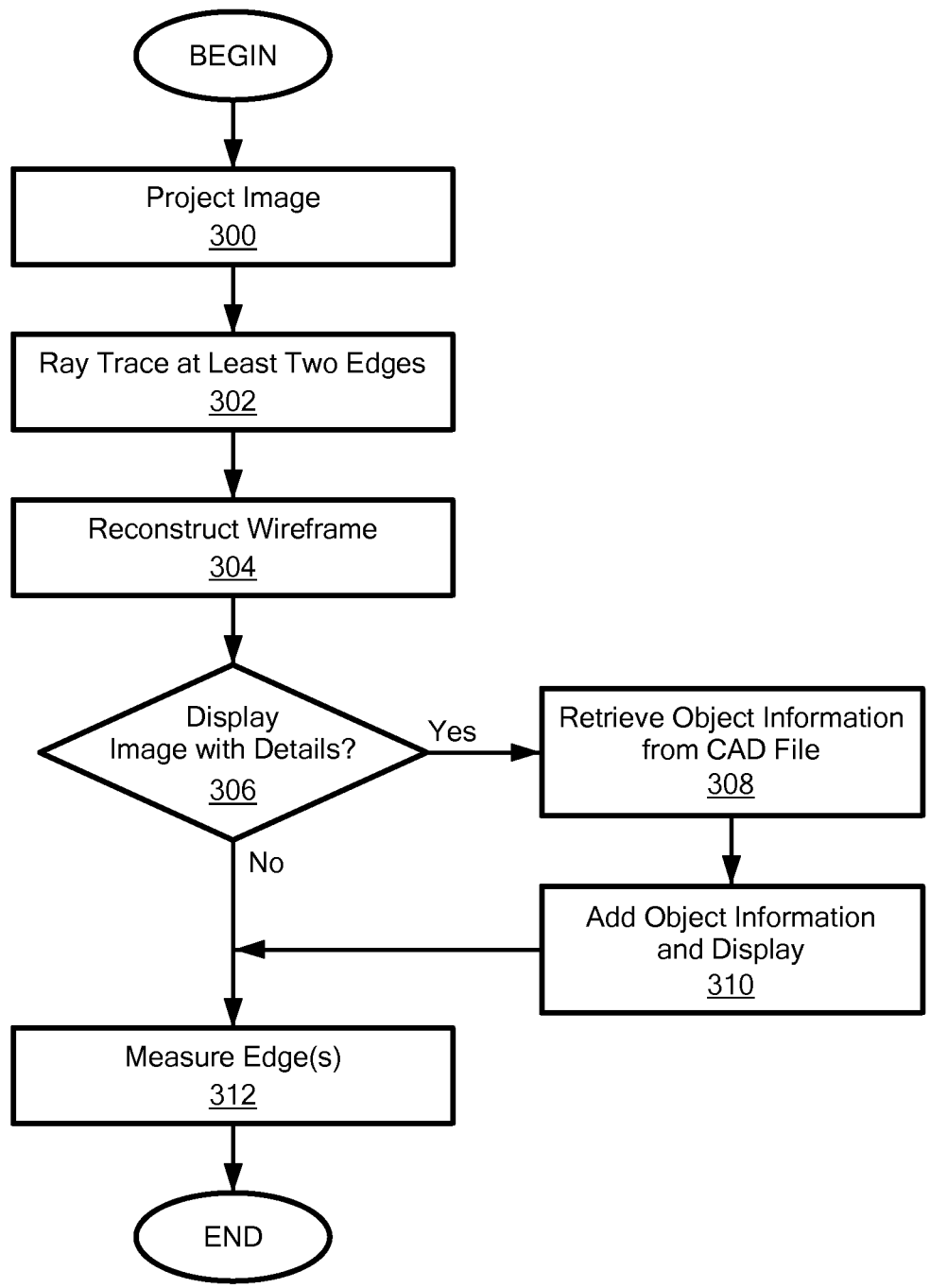
FIG. 3 shows a method of processing a projected image of an object in accordance with illustrative embodiments of the invention.

FIG. 3 shows how the internal logic of the apparatus of FIG. 2 collaborates to more efficiently measure the work piece 14 in accordance with illustrative embodiments of the invention. This process is a simplified version of a process that typically has more steps than those discussed. Instead, a reduced set of steps are discussed to simplify this discussion. Accordingly, the process may include intervening steps, or even omit certain steps. Moreover, those skilled in the art may modify the steps to change their order or otherwise non-materially alter the process. This flow of FIG. 3 therefore is intended as an exemplary process and not as the sole way of implementing illustrative embodiments.

FIGS. 4A-10 schematically show a plurality of figures that graphically illustrate the process used on a basic work piece 14 in the form of a cylinder, such as a stent or other similarly shaped object. It should be noted that discussion of such a work piece 14, however, is for illustrative purposes only and not intended to limit other embodiments of the invention. Instead, various embodiments can apply to many different objects, such as those having a geometry that is vastly different from that of a cylinder.

Figure 4B:
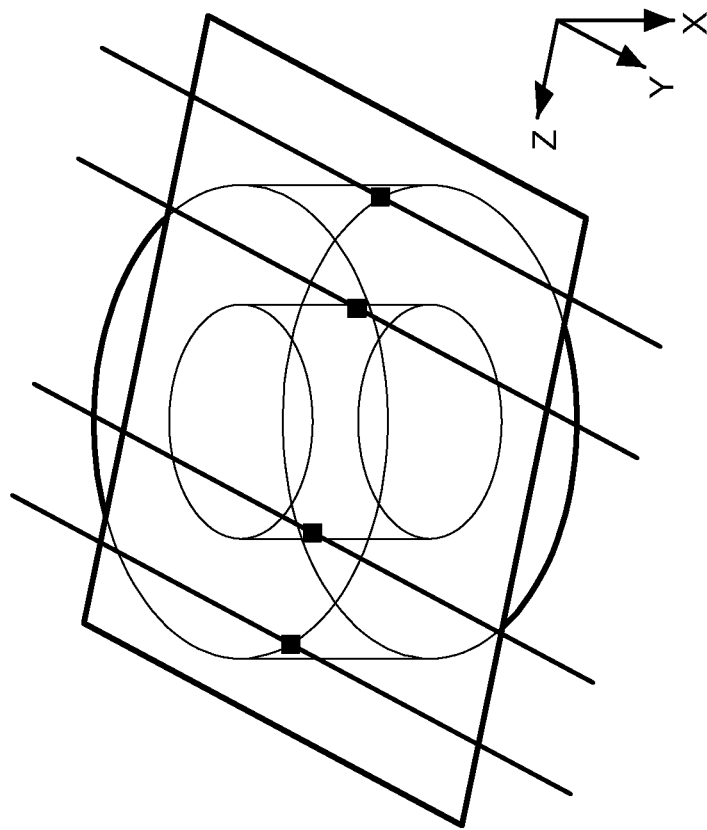
FIGS. 4A and 4B schematically show an exemplary object that may be processed in accordance with illustrative embodiments of the invention.
Figure 4A:
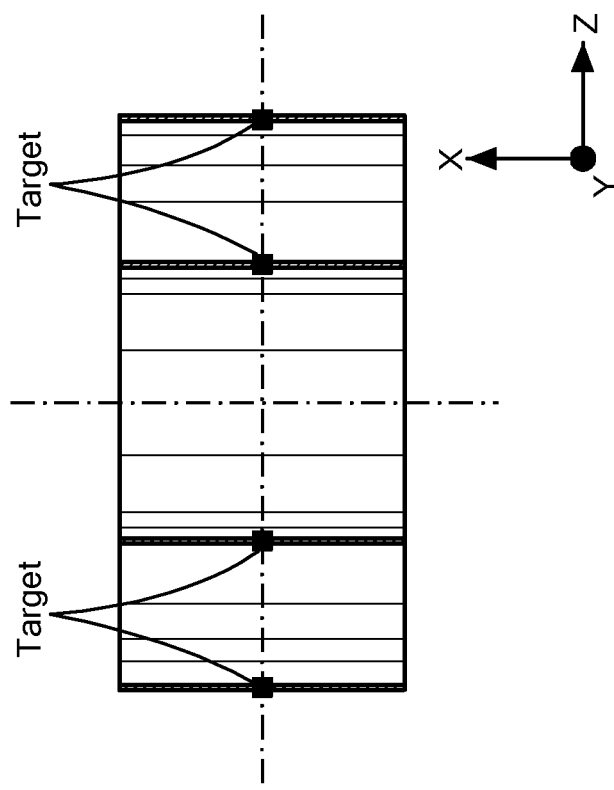

The process begins at step 300 by projecting an image of the work piece 14. In this case, the x-ray source 16 generates an x-ray beam/cone toward the work piece 14, which produces a projection image 40 on the detector 20. FIG. 4A schematically shows an example of how that projection may appear on the detector 20 as a translucent image.

Next, the process generates logical ray traces tangentially to least two edges of the work piece 14 (step 302). To that end, the edge detector 30 uses conventional edge detection algorithms to locate the edges of the work piece 14. Specifically, as known by those in the art, x-ray projection images 40 produced from x-ray systems may be digitized and processed in a manner that is similar to conventional vision systems. For example, many edge detection algorithms extract edge points from pixels within a sub-region of an image, or along a line where pixels lie. It also is possible to use a "best fit" standard two dimensional feature geometries, such as lines, circles, curves, etc. through the well-known process of "windowing." Such a process therefore preferably relies on nominal, known information (e.g., in a CAD file of the object) of where such edge features should be located based on the registration of the image with the object.

Unlike images taken by a camera or similar device, x-ray images may have edges in areas or edges of varying contrast due to overlapping materials (e.g., one region may be in front of the other from the perspective of the source 16), or because some such features/edges are internal to the object. Edges therefore may appear to overlap in any given projection view. In view of this, illustrative embodiments preferably use edge detection algorithms that detect such possible transitions in the image pixel map (i.e., in the image). Since the work piece 14 being processed is a known item, illustrative embodiments can use the nominal geometry information of the work piece 14, which may be within a CAD or other data file in the computer system 11 or other logic.

Figure 5:
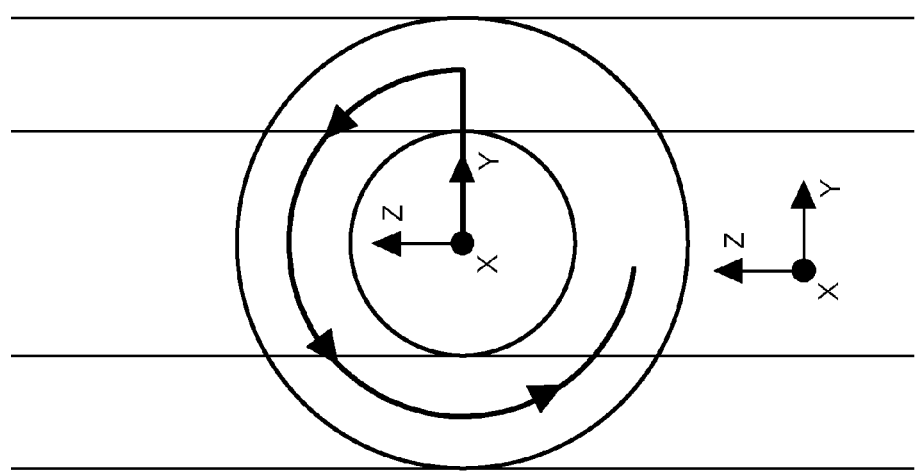

After the edges are detected, the ray tracer 32 may logically form rays that each are tangent to at least one edge of the work piece 14 (i.e., the object). In this embodiment, these rays extend from the source 16 through the image of the work piece 14. FIG. 4A schematically shows an example of this, with four rays extending through the work piece 14 (along the Y-axis from the perspective of the drawing). The word "tangent" and lead arrows show where each ray intersects an edge. FIG. 4B shows another view of the work piece 14, thus providing a view that better shows the work piece 14 and its tangent rays. FIG. 5 shows a top view of the work piece 14 and the rays extending along its edges.

The rays may be projected in one plane only, as shown in FIG. 4B, or along a plurality of parallel planes that are normal to the X-axis (e.g., 3 planes, 10 planes, hundreds of planes, or thousands of planes). A single plane having the rays in this example is shown in FIG. 4B. In this example of FIG. 4B, the plane is positioned somewhere between the top and bottom of the work piece 14. It should be noted that this figure still shows rays that are tangent to the work piece 14 despite the fact that the perspective drawing may appear to show some of the rays not being tangent. Specifically the two left-most rays may appear not to be tangent. However, that is a perspective drawing issue. Those two left-most rays are tangent as shown in FIG. 4A.

One skilled in the art can select the appropriate number of planes having rays based on a number of factors, including the time required to inspect the work piece 14, the desired final accuracy of the wireframe, and the total number of locations to measure the object.

Figure 6:
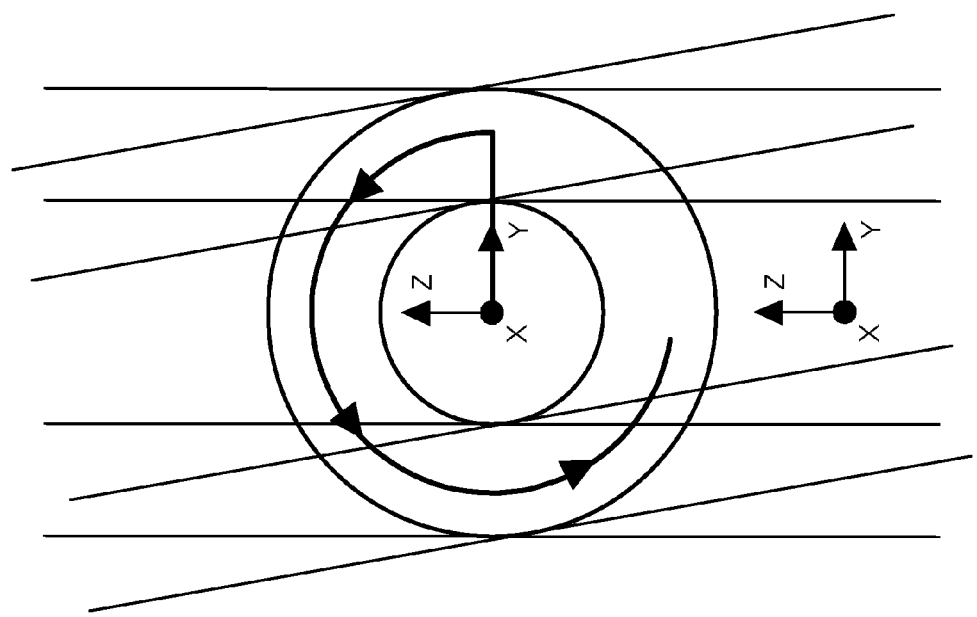
FIGS. 5 through 7 graphically show an example of the process of ray tracing along edges of the object of FIGS. 4A and 4B in accordance with illustrative embodiments of the invention.
Figure 7:
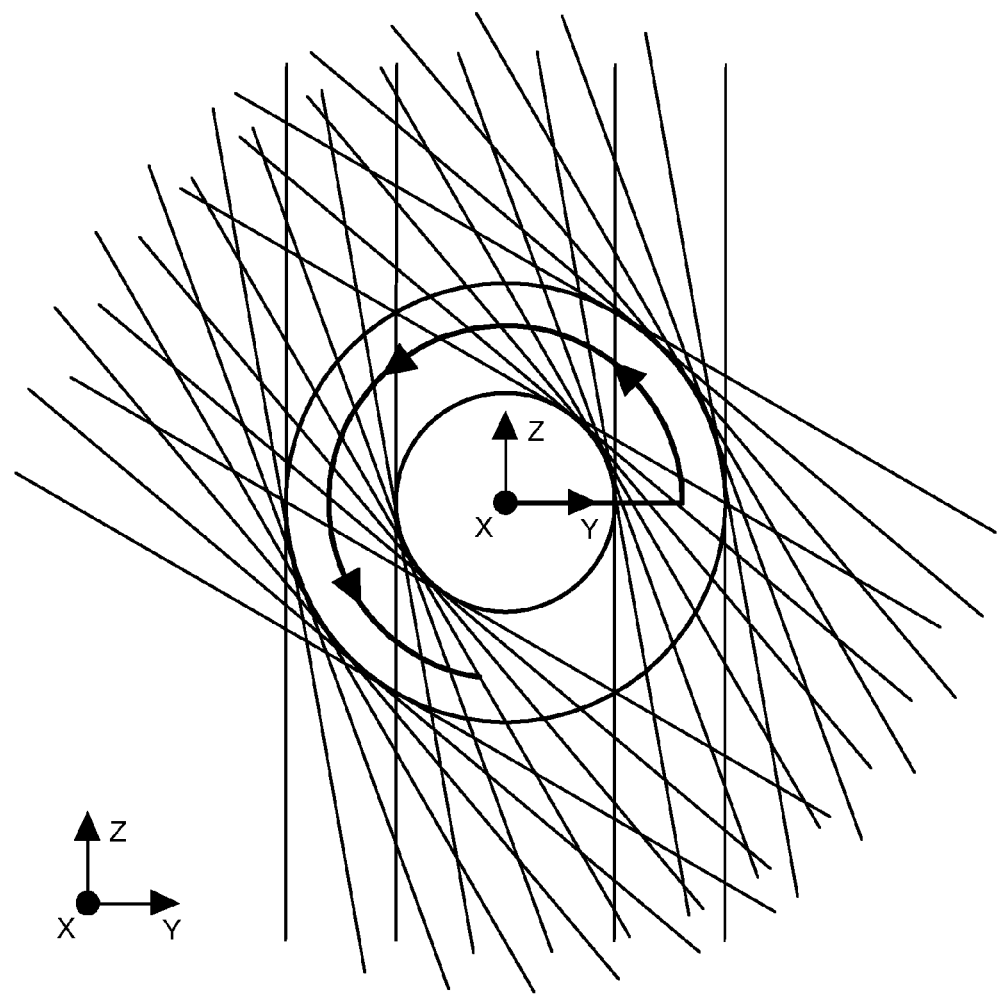
Figure 8:
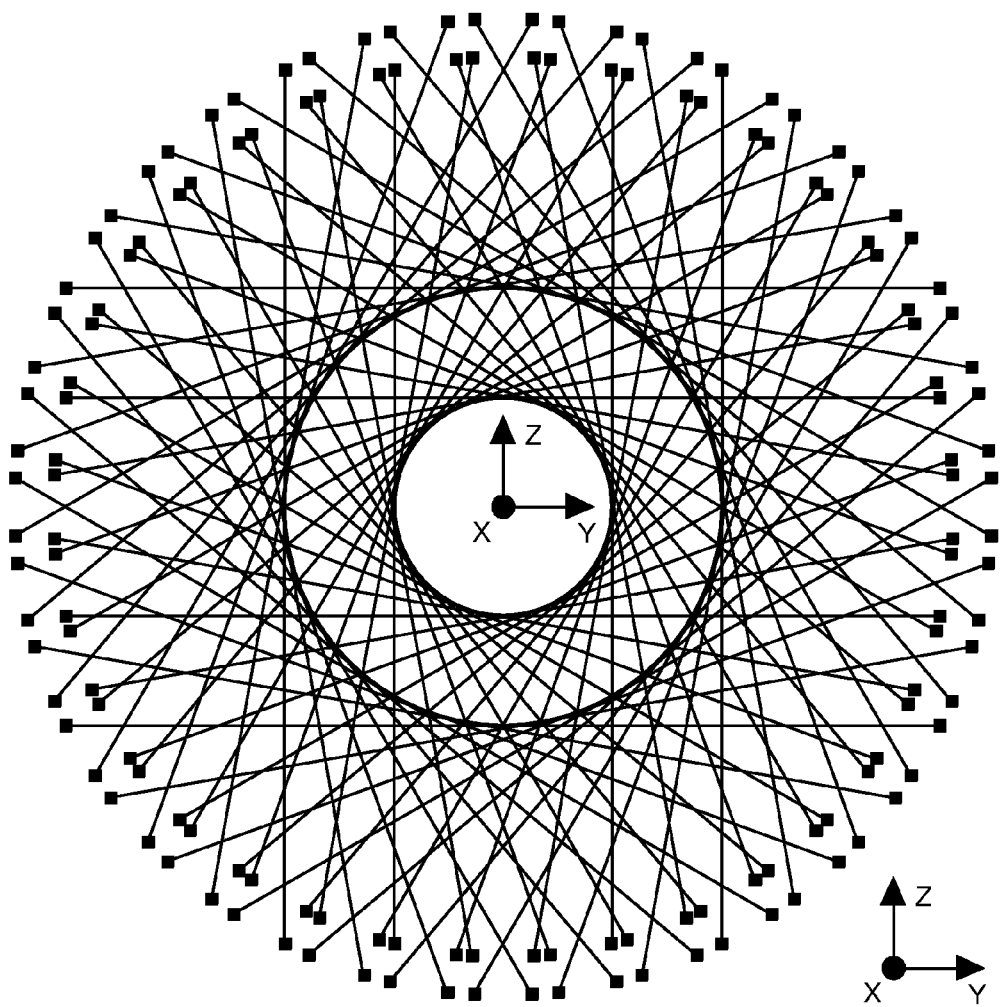
FIG. 8 graphically shows the process of using the ray traces of FIGS. 5 through 7 to form the edges of the object in accordance with illustrative embodiments of the invention.

The process repeats step 302 an appropriate number of times to generate enough different projection rays. Each projection is from a different orientation or angle relative to the object. FIGS. 6-8 schematically show additional projections as the work piece 14 rotates along its longitudinal axis on the rotary stage 18. In this case, the rotary stage 18 rotates the work piece 14 a full 360 degrees on its longitudinal axis so that the CT machine 10 can generate a high number of projections/images. Other embodiments, however, may take fewer images of the work piece 14. For example, the size and location of certain features, such as bosses and bores, may be nominally determined with a minimum number of views (e.g., two projections).

During imaging, the work piece 14 may rotate a prescribed amount (e.g., one degree or five degrees) and stop to be imaged. Some embodiments, however, may rotate the object generally continuously. Once imaged, rays can be applied to each image, ultimately approaching the many rays shown in FIG. 8. It should be noted that FIGS. 6-8 do not show actual rays. Instead, the reconstruction module 34 maintains a record of all the tangent points of the edges to logically construct the rays and projection of FIG. 8. This record may be stored in the memory 36 as the work piece 14 is imaged.

Figure 9:
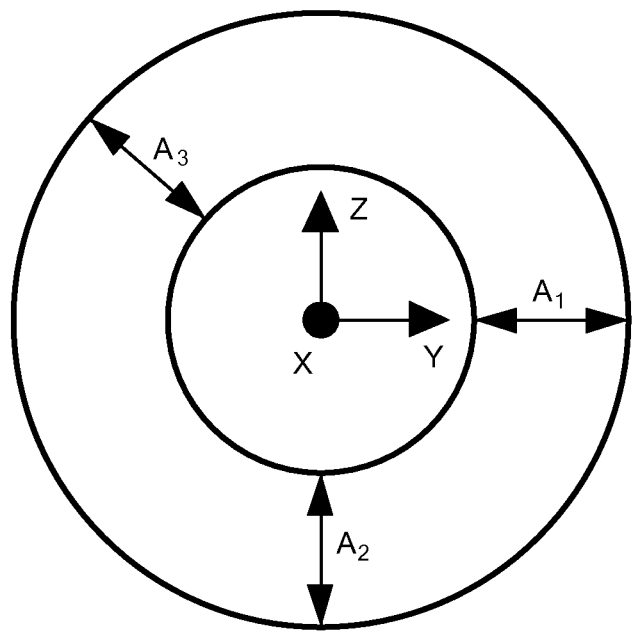
FIG. 9 graphically shows the wireframe edges of FIG. 8, and details between the wireframe edges in accordance with illustrative embodiments of the invention.

The process then continues to step 304, which reconstructs the wireframe of the object from these tangent points. FIGS. 9 and 10 graphically show how one embodiment completes this process. To that end, in illustrative embodiments, the reconstruction module 34 connects the tangent points of the rays at specified edges. As in FIG. 9, for the exemplary work piece 14, this step forms an inner edge (i.e., the inner circle) and an outer edge (i.e., the outer circle).

Problems can arise, however, when determining which sets of tangent points to connect together. In this example, the inner tangents are connected together, and the outer tangents are connected together. To that end, some embodiments may generate a point cloud of all tangents produced by the process. A filter (not shown) within the reconstruction module 34 then may apply an appropriate filtering process to aggregate appropriate tangents. Some such filtering processes may group tangent points based on their distances from each other. For example, such processes may group tangent points that are very close together into a single edge. Conversely, tangent points in small clusters spaced apart from one another may be excluded (these could reflect rays that intersect edges behind an edge of interest). These processes and filters also may make use of the CAD file of the work piece 14 to ensure that the correct tangent points are connected. Some embodiments, however, may not have an available CAD file.

At this stage, the process has a wireframe of the work piece 14. Some embodiments, however, do not produce a complete wireframe image. Instead, such embodiments produce a partial wireframe with just pre-specified portion of the work piece 14 needed for measurement purposes.

Next, the process determines whether to display the image, and if so, should that display have more detail than just the edges. If so, then the process continues to step 308, which retrieves information about the work piece 14 from the CAD file, and adds such information to the image for display on a display device (step 310). This image then may be forwarded to the display device, such as the monitor of the computer system 11, showing the edges and interior regions (e.g., textures, shapes, etc.). While the interior information may not be based on an actual inspection of the work piece itself, it can be enough to provide an appropriate look and feel.

The process then continues to step 312 (if not displaying or if displaying), in which the ruler 38 measures between the different edges of the 2D wireframe representation in memory 36. As shown in FIG. 9, the process can take any number of measurements, such as at locations A1, A2, and A3. These measurements can then be compared against the nominal CAD files to determine if the work piece dimensions are within prescribed tolerances. Some embodiments permit a user to select where to measure in real time. For example, a user may select certain work piece dimension to measure by selecting certain points on the displayed image on the monitor of the computer system 11.

If rays are produced in only one plane normal to the X-axis, then this process can be repeated many times in rapid succession to produce a 3D wireframe model as shown in FIG. 10. Specifically, logic can simply connect the vertices of the different 2D wireframe models using CAD data or by some other means. Alternatively, some embodiments produce a 3D wireframe model in a similar manner if rays are produced in multiple parallel planes normal to the X-axis. Either way, like step 312, the ruler 38 can measure at multiple different locations, such as at M1, M2, and M3. Also like steps 308 and 310, this wireframe model can use stored CAD information to display the object on a display device.

In an assembly line, due to the significant volume of data they had to read and generate, prior art non-contact x-ray based metrological inspection processes became a significant congestion point, ultimately reducing the speed at which a part could be produced. Illustrative embodiments overcome this problem by imaging only the portions of the part that require measurements—in this case, the edges. Some embodiments may select portions other than the edges, such as concave region. In any event, imaging and reconstructing only the required portions should decrease processing time, improving part throughput. Accordingly, such embodiments improve the function of the system itself.

Various embodiments of the invention may be implemented at least in part in any conventional computer programming language. For example, some embodiments may be implemented in a procedural programming language (e.g., "C"), or in an object oriented programming language (e.g., "C++"). Other embodiments of the invention may be implemented as preprogrammed hardware elements (e.g., application specific integrated circuits, FPGAs, and digital signal processors), or other related components.

In an alternative embodiment, the disclosed apparatus and methods (e.g., see the various flow charts described above) may be implemented as a computer program product for use with a computer system. Such implementation may include a series of computer instructions fixed either on a tangible, non-transitory medium, such as a computer readable medium (e.g., a diskette, CD-ROM, ROM, or fixed disk). The series of computer instructions can embody all or part of the functionality previously described herein with respect to the system.

Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies.

Among other ways, such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). In fact, some embodiments may be implemented in a software-as-a-service model ("SAAS") or cloud computing model. Of course, some embodiments of the invention may be implemented as a combination of both software (e.g., a computer program product) and hardware. Still other embodiments of the invention are implemented as entirely hardware, or entirely software.

Although the above discussion discloses various exemplary embodiments of the invention, it should be apparent that those skilled in the art can make various modifications that will achieve some of the advantages of the invention without departing from the true scope of the invention.

What is claimed is:

1. A system for measuring an object, the system comprising:

a chamber sized to receive and contain an object;

an x-ray source within the chamber, the x-ray source being movable relative to the object within the chamber, the x-ray source being configured to project a plurality of x-ray images of an object, at least two of the plurality of x-ray images being projected from different directions relative to the object, the object having at least two edges;

an edge detector configured for locating the at least two edges in the x-ray images;

a ray tracer operatively coupled with the edge detector, the ray tracer being configured to ray trace a plurality of lines, each ray traced line being tangent to at least one point on at least one located edge;

a reconstruction module operatively coupled with the ray tracer, the reconstruction module being configured to reconstruct at least a partial wireframe model of the object from the tangent points of the ray traced lines, the wireframe model including the at least two edges; and a ruler operatively coupled with the reconstruction module to receive the at least partial wireframe model, the ruler being configured to measure between the at least two edges of the at least partial wireframe model.

2. The system as defined by claim 1 wherein the edge detector is configured to receive and determine the location of the edges in response to receipt of a digital file containing a digital model of the object.

3. The system as defined by claim 2 wherein the digital file comprises a computer aided design file.

4. The system as defined by claim 1 wherein the wireframe model is a 2D image.

5. The system as defined by claim 1 wherein at least one of the edges is interior to the object.

6. The system as defined by claim 1 wherein ray tracer is configured to produce a plurality of points that each are tangent to at least one of the edges, the reconstruction module being configured to access information relating to the edges and selectively connect sets of the plurality of points to produce the at least two edges in the wireframe model.

7. A method of measuring an object, the method comprising:

projecting, using an x-ray source, a plurality of x-ray images of an object, at least two of the plurality of x-ray images being projected from different directions relative to the object, the object having at least two edges;

locating the at least two edges in the x-ray images;

ray tracing a plurality of lines, each ray traced line being tangent to at least one point on at least one of the located edges;

reconstructing at least a partial wireframe model of the object from the tangent points of the ray traced lines, the wireframe model including the at least two edges; and measuring between the at least two edges of the at least partial wireframe model.

8. The method as defined by claim 7 wherein locating the at least two edges comprises accessing a digital file containing a digital model of the object.

9. The method as defined by claim 8 wherein the digital file comprises a computer aided design file.

10. The method as defined by claim 8 further comprising: generating a 3D image of the object using the digital file and the wireframe model; and transmitting the 3D image toward a display device for display.

11. The method as defined by claim 7 further comprising positioning the object in an interior chamber of an x-ray computed tomography machine.

12. The method as defined by claim 7 wherein the wireframe model is a 2D image.

13. The method as defined by claim 7 wherein at least one of the edges is interior to the object.

14. The method as defined by claim 7 wherein ray tracing produces a plurality of points that each are tangent to at least one of the edges, reconstructing comprising accessing information relating to the edges and selectively connecting sets of the plurality of points to produce the at least two edges in the wireframe model.

15. The method as defined by claim 14 wherein the plurality of points comprises a first set of points and a second set of points, the first set of points being connected to represent a first edge of the object, the second set of points being connected to represent a second edge of the object.

16. The method as defined by claim 7 further comprising applying a filtering process to aggregate tangents.

17. A computer program product for use on a computer system for measuring an object, the computer program product comprising a tangible, non-transient, computer-readable medium having computer readable program code thereon, the computer readable program code comprising:

program code for causing an x-ray source to project a plurality of x-ray images of an object within an interior chamber of an x-ray machine, at least two of the plurality of x-ray images being projected from different directions relative to the object, the object having at least two edges;

program code for locating the at least two edges in the x-ray images;

program code for ray tracing a plurality of lines, each ray traced line being tangent to at least one point on at least one of the located edges;

program code for reconstructing at least a partial wireframe model of the object from the tangent points of the ray traced lines, the wireframe model including the at least two edges; and program code for measuring between the at least two edges of the at least partial wireframe model.

18. The computer program product as defined by claim 17 wherein program code for locating the at least two edges comprise program code for accessing a digital file containing a digital model of the object.

19. The computer program product as defined by claim 18 further comprising:

program code for generating a 3D image of the object using the digital file and the wireframe model; and program code for transmitting the 3D image toward a display device for display.

20. The computer program product as defined by claim 17 wherein at least one of the edges is interior to the object.

21. The computer program product as defined by claim 17 wherein the program code for ray tracing produces a plurality of points that each are tangent to at least one of the edges, the program code for reconstructing comprising program code for accessing information relating to the edges and selectively connecting sets of the plurality of points to produce the at least two edges in the wireframe model.

* * * * *